(12) United States Patent
Saccomanno

(10) Patent No.: US 6,594,009 B2
(45) Date of Patent: Jul. 15, 2003

(54) FLOW CYTOMETER AND ULTRAVIOLET LIGHT DISINFECTING SYSTEMS

(75) Inventor: Robert J. Saccomanno, Montville, NJ (US)

(73) Assignee: Honeywell International Inc., Morristown, NJ (US)

(*) Notice: Subject to any disclaimer, the term of this patent is extended or adjusted under 35 U.S.C. 154(b) by 0 days.

(21) Appl. No.: 10/008,487

(22) Filed: Nov. 5, 2001

(65) Prior Publication Data

US 2002/0118362 A1 Aug. 29, 2002

Related U.S. Application Data

(60) Provisional application No. 60/271,885, filed on Feb. 27, 2001, and provisional application No. 60/297,387, filed on Jun. 11, 2001.

(51) Int. Cl.[7] ................................................. G01N 1/10
(52) U.S. Cl. ........................... 356/246; 356/244; 362/32
(58) Field of Search ............................... 356/244, 246, 356/336, 337, 338, 339, 340, 341, 342, 343, 318.317, 73; 250/461.2; 362/32, 298, 346

(56) References Cited

U.S. PATENT DOCUMENTS

| 3,946,239 A | * | 3/1976 | Salzman et al. ............ 250/461 |
|---|---|---|---|
| 4,017,163 A | | 4/1977 | Glass |
| 4,084,887 A | | 4/1978 | Sigler |
| 4,179,192 A | | 12/1979 | Shafer |
| 4,188,543 A | * | 2/1980 | Brunsting et al. .......... 356/318 |
| 4,189,236 A | | 2/1980 | Hogg et al. |
| 4,200,802 A | * | 4/1980 | Salzman et al. ............ 356/318 |
| 4,348,107 A | * | 9/1982 | Leif ........................... 356/246 |
| 4,412,742 A | * | 11/1983 | Lloyd .......................... 356/73 |
| 4,657,721 A | | 4/1987 | Thomas |
| 5,321,586 A | * | 6/1994 | Hege et al. ..................... 362/32 |
| 5,414,508 A | * | 5/1995 | Takahashi et al. .......... 356/246 |
| 5,446,289 A | | 8/1995 | Shodeen et al. |
| 5,494,576 A | | 2/1996 | Hoppe et al. |
| 5,504,335 A | | 4/1996 | Maarschalkerweerd |
| 5,560,699 A | * | 10/1996 | Davenport et al. ............ 362/32 |
| 5,684,575 A | | 11/1997 | Steen |
| 5,785,845 A | | 7/1998 | Colaiano |
| 5,832,361 A | | 11/1998 | Foret |
| 5,946,091 A | * | 8/1999 | Yufa ........................... 356/336 |
| 5,952,663 A | | 9/1999 | Blatchley, III et al. |
| 5,999,250 A | * | 12/1999 | Hairston et al. ............. 356/318 |

OTHER PUBLICATIONS

Guidelines for Drinking Water Quality, vol. 1, World Health Organization, Geneva, Switzerland, 1993, p. 135.

* cited by examiner

Primary Examiner—Frank G. Font
Assistant Examiner—Sang H. Nguyen

(57) ABSTRACT

An optical system including a unique mirror arrangement surrounding a tube containing a flowing fluid with suspended biological material can be configured as flow cytometer or as an ultraviolet light disinfecting system. The optical system includes a plurality of off-axis ellipsoidal mirrors defining first and second focal points; the first focal point is coincident with a flow tube extending through the optical system. Multifunction optical units are located at the second focal points of the ellipsoidal mirrors. High intensity excitation light impinges on the material flowing through the flow tube.

20 Claims, 4 Drawing Sheets

Flow direction is into page

FLOW CYTOMETER AND ULTRAVIOLET LIGHT DISINFECTING SYSTEMS

CROSS-REFERENCE TO RELATED APPLICATIONS

This application claims priority from U.S. Provisional Patent Application Serial No. 60/271,885 entitled, "Flow Cytometer Optical Arrangement", filed on Feb. 27, 2001. The contents of U.S. Provisional Patent Application Serial No. 60/271,885 are fully incorporated herein by reference and also Ser. No. 60/297,387 filed Jun. 11, 2001.

An optical system, including off-axis ellipsoidal mirrors, suitable for application in the present invention is described in U.S. patent application Ser. No. 09/346,253, entitled "Display System Having a Light Source Separate from a Display Device".

FEDERALLY SPONSORED RESEARCH OR DEVELOPMENT

Not Applicable

BACKGROUND OF THE INVENTION

1. Technical Field

This invention relates to an optical apparatus suitable for use with a flowing fluid containing biological cells and more specifically to flow cytometry, the measurement of the fluorescence and light scattering of individual biological cells and other types of microscopic particles.

2. Background Art

As described in Steen, U.S. Pat. No. 5,684,575, a flow cytometer is an instrument for measurement of the fluorescence and light scattering of individual biological cells and other types of microscopic particles.

Hogg et al., U.S. Pat. No. 4,189,236, teaches the placement of a biological sample within an enclosed reflector cavity where part of the cavity is removed in order to facilitate placement of a focusing mirror. A limitation of the Hogg approach is that it requires a high numerical aperture (NA) for both the sensor and the excitation source. Also, the Hogg apparatus requires complex coupling optics and only has a single sensor port.

Ultraviolet (UV) light is known to be useful to disinfect fluids such as air and water by killing of bacteria, viruses and other pathogens. Specifically, ultraviolet (UV) light with a wavelength of between 100 nanometers (nm) to 280 nm, known in the art as 'UV-C', is known to be germicidal. UV-C light is known to deactivate the deoxyribonucleic acid (DNA) contained within bacteria, viruses and other pathogens thus destroying their ability to multiply and cause disease. UV-C light with a wavelength of approximately 260 nm provides the highest germicidal effectiveness.

For most water borne pathogens, exposure to UV-C light with an energy flux of 20 milliwatt-seconds/cm$^2$ is adequate to deactivate 99 percent of these pathogens. The World Health Organization (WHO) has a recommended standard of performance for an acceptable water disinfecting system that requires the processing of contaminated water containing 100,000 colony forming units (CFU) of *e-coli* bacteria per 100 ml of water and producing outlet water with less than one CFU per 100 ml. *Guidelines for Drinking Water Quality*, vol. 1, World Health Organization, Geneva, Switzerland, 1993, pg. 135.

The traditional approach in UV disinfecting systems is to use low-pressure mercury discharge lamps (i.e. fluorescent lamp without the phosphor). These lamps provide relatively low intensity energy flux, therefore to handle high fluid flow rates many such lamps are required along with large volume fluid storage tanks.

There is a long felt need in the art of flow cytometry for improved detection sensitivity, such as when there are but a few biological cells present in the flowing fluid. In addition, there is a long felt need in general for a safe and reliable method of disinfecting drinking water for human consumption using ultraviolet radiation.

SUMMARY OF THE INVENTION

My invention is a flow cytometer device where a fluid a fluid flows through this device and is illuminated by light or other radiation. The interaction with the flowing fluid and the light is detected by sensors within the flow cytometer. More specifically, my invention is directed toward an optical system making up part of the overall flow cytometer device.

The optical system according to my invention provides several unique enhancements to traditional flow cytometry. Advantageously, my inventive apparatus increases the collection efficiency of the fluorescent energy, for example from a biological cell, thereby enhancing the signal/noise ratio of a detected signal. A flow cytometer according to my invention can use simple sensors, such as photo-multiplier tubes (PMT), or imaging-based sensors such as charge-coupled devices (CCD) and can also provide a full 360 degree view of the specimen, potentially leading to a three dimensional capability.

The optical system according to my invention can additionally be used to disinfect a flowing fluid such as water by focussing ultraviolet light on the flowing fluid and thereby killing biological cells contained in the fluid.

BRIEF DESCRIPTION OF DRAWINGS

FIG. 2, in particular, illustrates the inside mirror surface of several off-axis ellipsoidal mirrors.

FIG. 4, in particular, illustrates the outside mirror surface of several off-axis ellipsoidal mirrors.

DETAILED DESCRIPTION OF THE INVENTION

Mode(s) for Carrying Out the Invention

Figure 1:
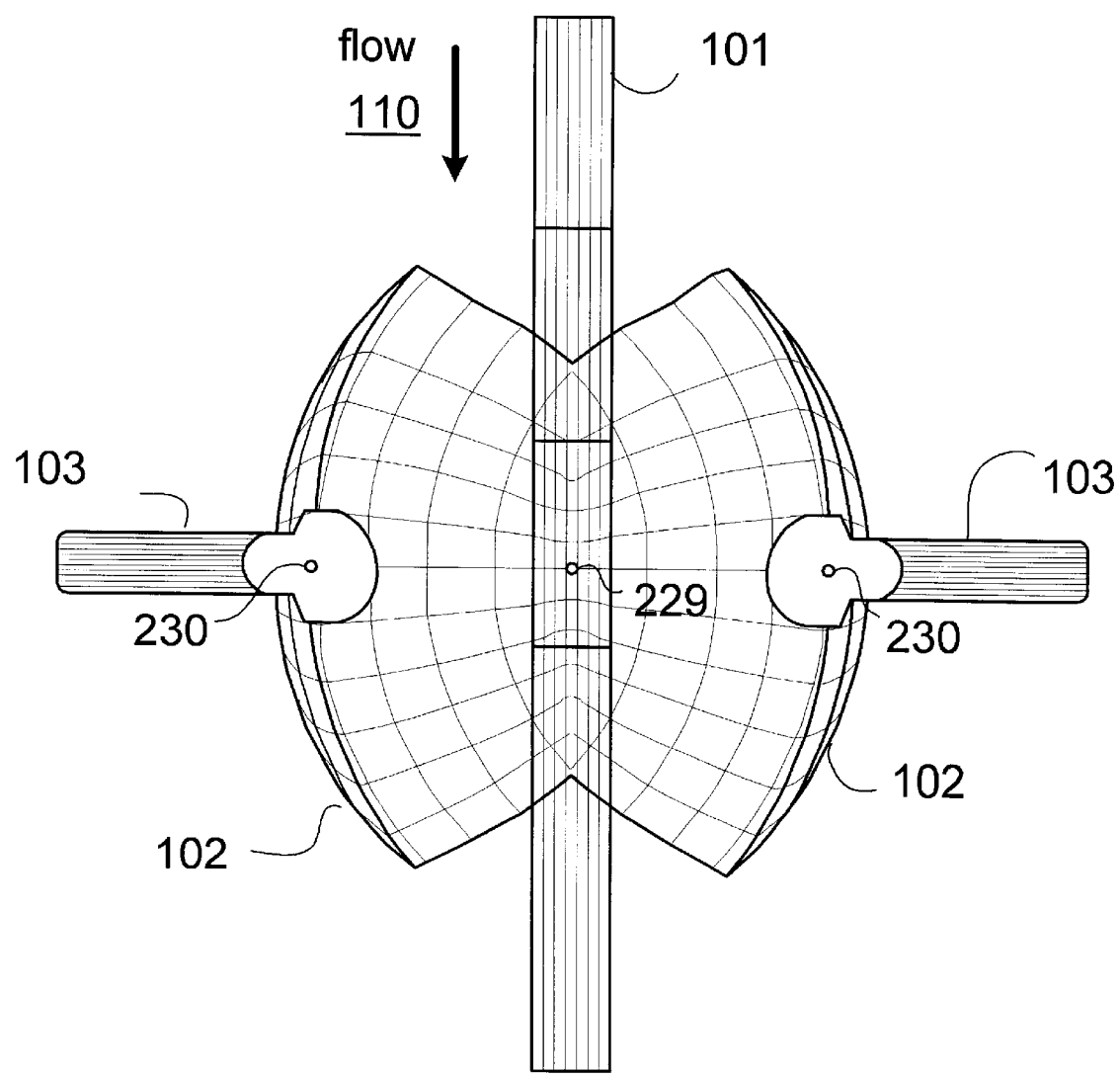
FIG. 1 depicts a cutaway view of a flow cytometer and ultraviolet light disinfecting system, along a flow axis, in accordance with one illustrative embodiment of my invention.

Referring to FIG. 1, a flow tube 101 designed to carry biological material suspended in a flowing fluid 110, such as water traveling in a predetermined flow direction is surrounded by off-axis ellipsoidal mirrors 102 and multifunction optical units 103. Each multifunction optical unit 103 can include an imaging or non-imaging optical detector and an optical excitation source, such as an ultraviolet (UV) light. When my inventive optical configuration is used as a flow cytometer, at least one of the multifunction optical units 103 must contain an optical detector.

Each off-axis ellipsoidal mirror 102 defines a first and a second focal point, where the first focal point 229 of each off-axis ellipsoidal mirror 102 is coincident upon the flow tube 101 and the second focal point 230 of each off-axis ellipsoidal mirror 102 is coincident upon a corresponding multifunction optical unit 103. Each of the distinct second focal points 230, seen in FIG. 2, is located at a small port between opposing off-axis ellipsoidal mirrors 102.

Figure 2:
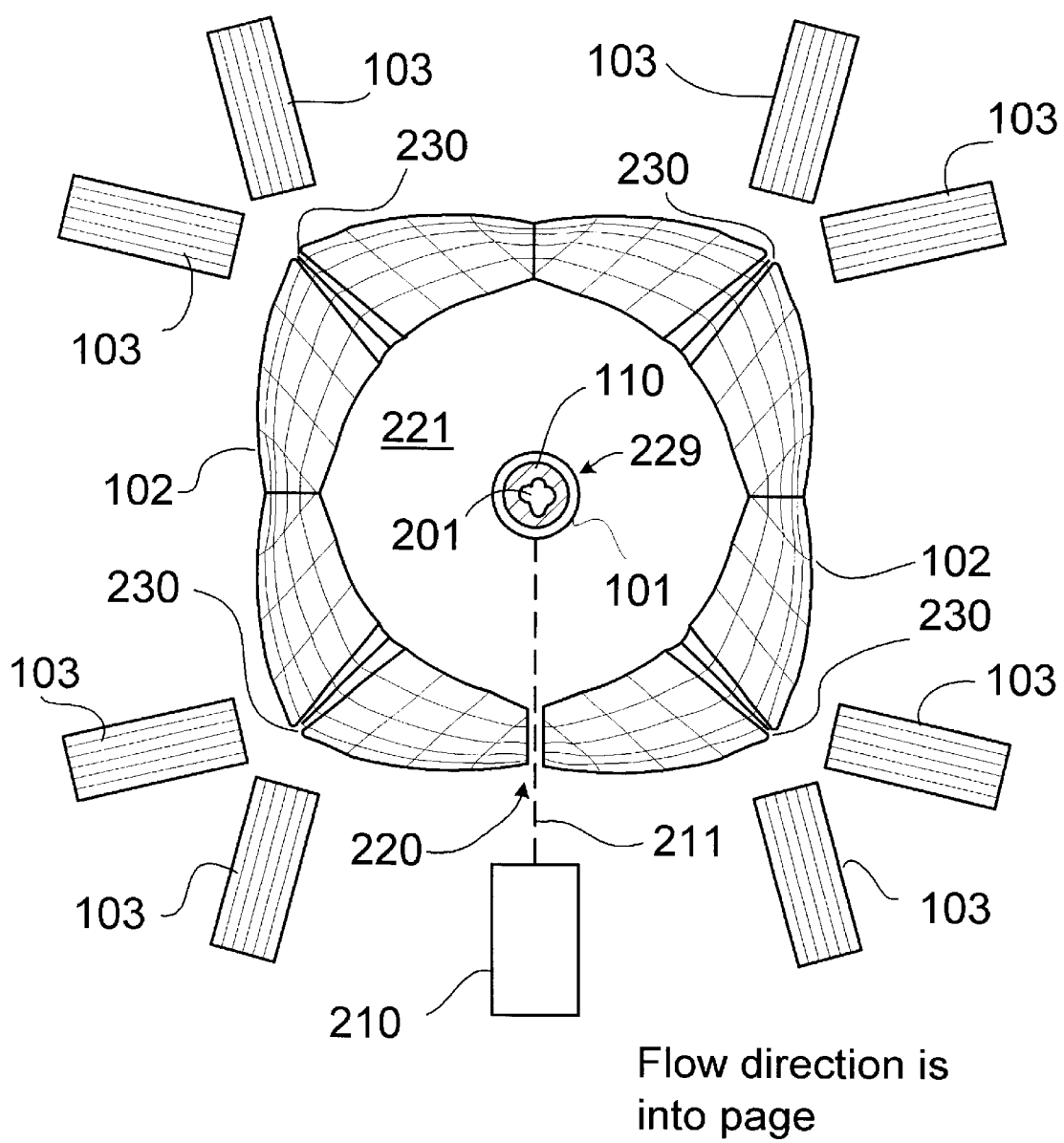
FIG. 2 depicts a cutaway view of the flow cytometer and ultraviolet light disinfecting system of FIG. 1, across a flow axis.

Referring next to FIG. 2, the flowing fluid 110, contained within the flow tube 101, carries a sample of biological material 201. In one embodiment of my invention, the sample of biological material 201 is selectively irradiated by high-intensity light 211, such as a laser beam, emanating from an external light source 210, such as a laser. The laser beam can be introduced into an internal mirror cavity 221, defined by the individual off-axis ellipsoidal mirrors 102, through a small aperture 220 in one of the off-axis ellipsoidal mirrors 102. This laser irradiation can cause the biological material 201, contained within the sample, to fluoresce and emit light energy. The light energy emitted from the biological material 201 reflects from the off-axis ellipsoidal mirrors 102, impinges upon, and is detected by the multifunction optical units 103. For certain biological materials 201, a dye is added to the flowing fluid 110 to stain cells contained within the biological material 201.

Figure 3:
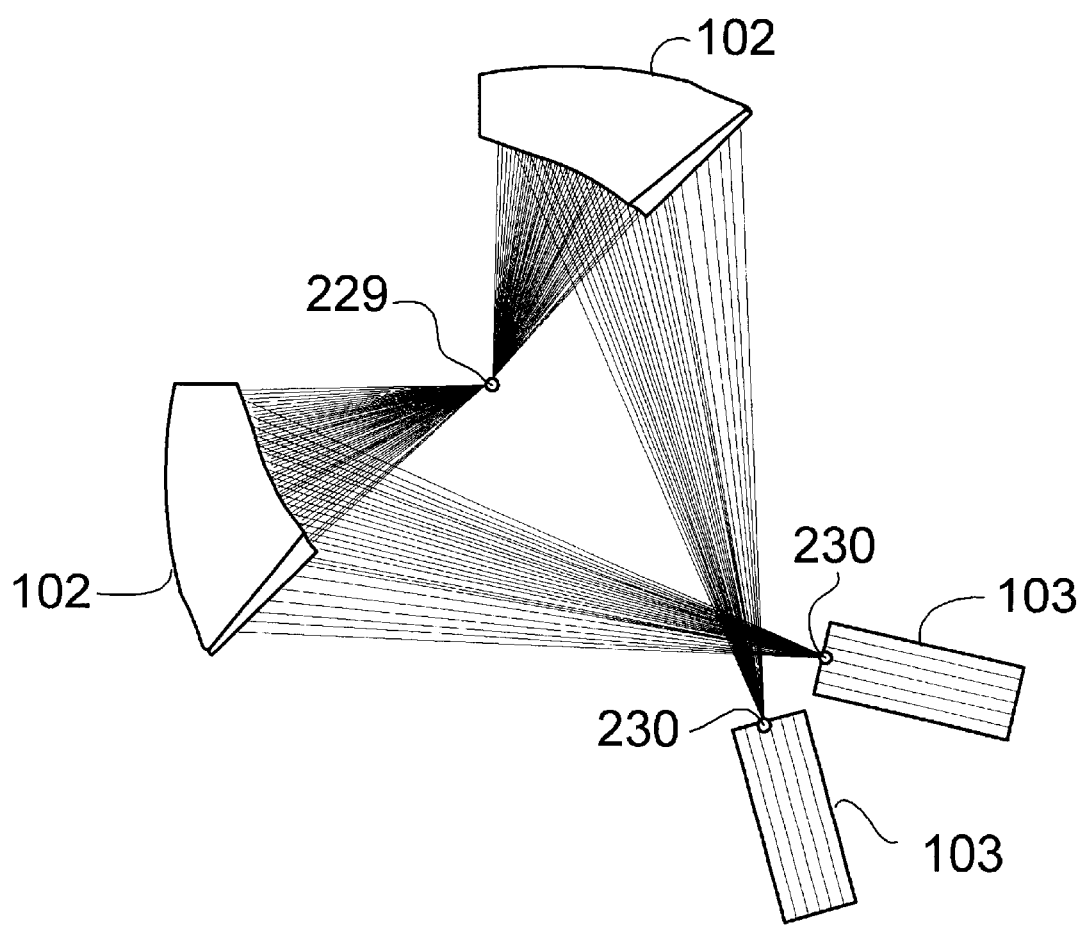
FIG. 3 further details the coincident first focal points 229 and distinct second focal points 230 for two of the off-axis ellipsoidal mirrors 102 shown in FIG. 2.
Figure 4:
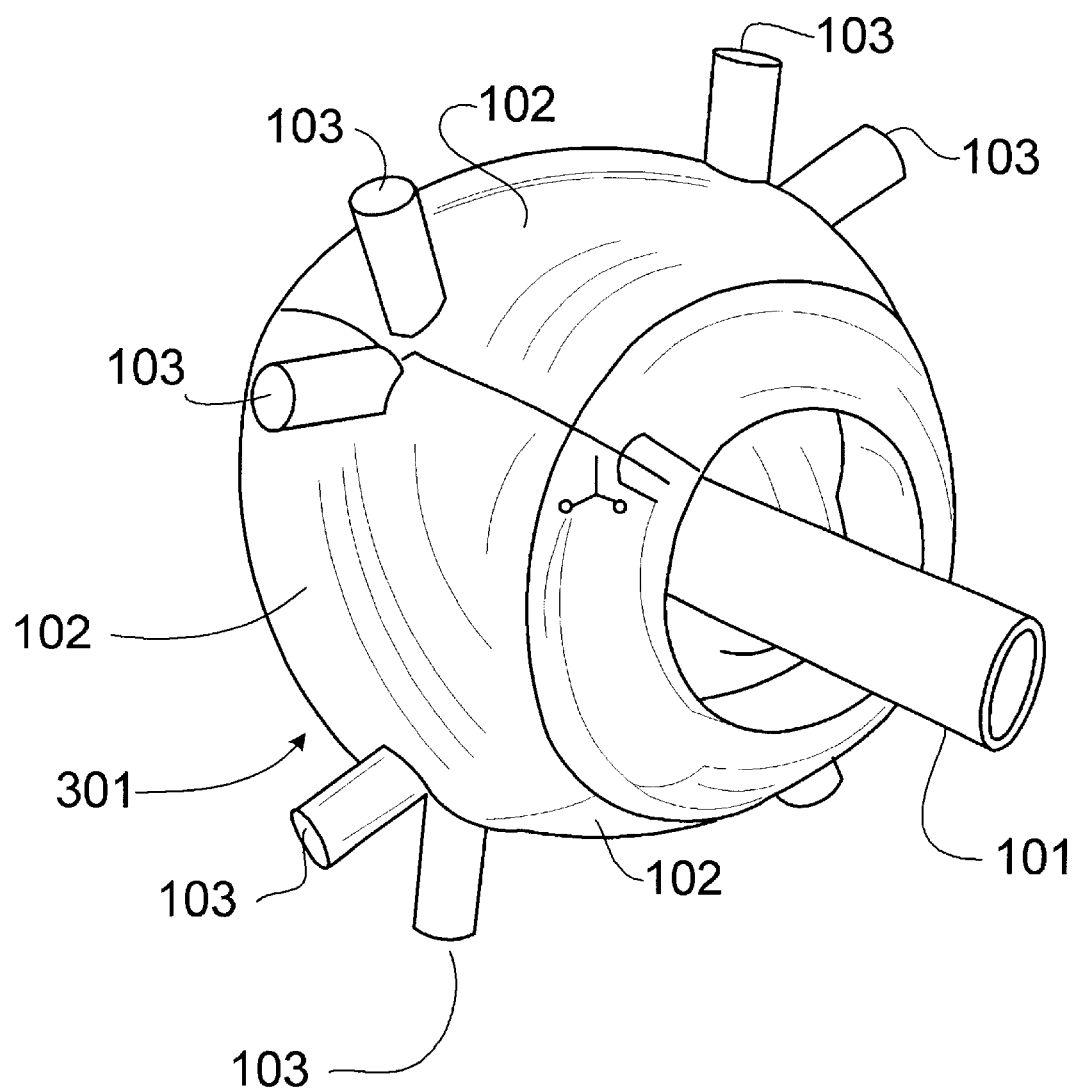
FIG. 4 depicts an isometric view of the mirrors surrounding a flow tube, for the flow cytometer and ultraviolet light disinfecting system of FIG. 1.

FIG. 3 further details the coincident first focal points 229 and distinct second focal points 230 for two of the off-axis ellipsoidal mirrors 102 shown in FIG. 2.

To operate the flow cytometer according to my invention, a sample of biological material 201 is carried by the flowing fluid 110, such as a laminar flow of water, through a high intensity light source. Each biological cell passing through the high-intensity light source will emit a short pulse of fluorescence and scattered light. The cells, within the sample of biological material 201 can be advantageously stained with a fluorescent dye, which can selectively bind to a particular cell constituent. The intensity of the fluorescence will be proportional to the cellular content of fluorescent dye and thereby with the cellular content of the stained constituent. The intensity of the scattered light and its angular distribution is a complex function of the size, shape, structure and chemical composition of the cell. By detecting and measuring, with a plurality of multifunction optical units 103, the light scattering at small and large scattering angles, respectively, it is thus possible to distinguish biological cells based on size, shape, and structure.

Other embodiments of my invention couple the external light source 210, through a fiber optic cable to the aperture 220, thus ameliorating heat concerns near the biological specimen 201 contained within the flowing fluid 110. In further embodiments of my invention, a plurality of external light sources 210 and apertures 220 are used to illuminate the sample of biological material 201, with each external light source 210 advantageously providing a different unique excitation wavelength band.

Referring next to FIG. 3, an isometric view of the mirror and flow tube arrangement described previously is shown. An optical mirror enclosure 301, formed from the several off-axis ellipsoidal mirrors 102 and defining the internal mirror cavity 221, fully surrounds the flow tube 101 as previously described. The flow tube 101, containing the biological material 201 passes through the optical mirror enclosure 301, such that the biological material 201 passes through the common, first focal point 229 of the off-axis ellipsoidal mirrors 102.

The flow tube 101 has two ends that protrude from opposing ends of the mirror enclosure 301. The first end of the flow tube 101 is connected to a supply of the flowing fluid 110, such as a public water supply reservoir. The second end of the flow tube 101, containing a disinfected flowing fluid, can be connected, for example, as an inlet to a public water supply pipeline.

In a preferred embodiment of my invention, the optical mirror enclosure 301 is constructed from the off-axis ellipsoidal mirrors 102 in the following manner. First, the off-axis ellipsoidal mirrors 102 are compliantly fastened and aligned to a central hub through the use of garter springs. Next, the bottom surface edge of each off-axis ellipsoidal mirror 102 is spring-loaded from the bottom such that the top surface edge of all the off-axis ellipsoidal mirrors 102 bottom out on a common top cover-plate.

Referring back to FIG. 2, in another illustrative embodiment of my invention, the biological material 201 is illuminated by a light source contained within one of the multifunction optical units 103 located at the second focal 230 point of one of the off-axis ellipsoidal mirrors 102. The resulting fluorescence is detected and measured by the remaining multifunction optical units 103 which are each located at the second focal points 230 of the remaining off-axis ellipsoidal mirrors 102.

Advantageously, each of multifunction optical units 103, which are located at the second focal point 230 of the off-axis ellipsoidal mirrors 102, can incorporate an excitation source and an optical detector. The optical detectors can be simple non-imaging sensors such as photodiodes or photo-multiplier tubes (PMT) or more complex imaging devices such as charge coupled devices (CCD), complementary metal oxide semiconductor (CMOS) array sensors, or image intensifying tubes (IIT).

In one alternative embodiment of my invention, the multifunction optical units 103 include fiber optic cables coupled between exit ports of the mirror cavity 221, where each exit port is located at the second focal point 230 of a corresponding off-axis ellipsoidal mirror 102. This alternate embodiment advantageously allows for flexible packaging alternatives.

In further embodiments of my invention, the surfaces of the off-axis ellipsoidal mirrors 102 are coated with materials having specific optical properties, such as broadband mirror coatings, notch filter coatings or metallized coatings.

Advantageously, my invention can be configured as an extremely compact flow cytometer unit, which can allow for a high degree of portability, including, for example, a handheld flow cytometer unit with a high-resolution liquid crystal display (LCD) screen.

Advantageously, my inventive optical configuration can also be used to disinfect the flowing fluid 110. In alternate embodiments of my invention, the multifunction optical units 103 include high-intensity ultraviolet (UV) light sources, such as UV-C light source, with a wavelength of approximately 260 nanometers (nm). In one alternate embodiment of my invention, each multifunction optical unit 103 includes a low-pressure mercury discharge lamp.

In another embodiment of my invention, at least one of multifunction optical units 103 includes high-intensity ultraviolet (UV) light sources to disinfect the fluid flow by killing the biological material and at least one of the of multifunction optical unit 103 includes an optical detector to monitor the disinfecting process.

Alternate embodiments may be devised without departing from the spirit or the scope of the invention.

What is claimed is:

1. An optical system for use in conjunction with a flowing fluid containing suspended biological material, said optical system comprising:

a flow tube, designed to carry said flowing fluid, and including a first and a second end;

a plurality of off-axis ellipsoidal mirrors forming an optical mirror enclosure and defining an internal mirror cavity, wherein said internal cavity fully surrounds said flow tube and the first and second ends of said flow tube protrude from opposing sides of said optical mirror enclosure, wherein each of said off-axis ellipsoidal mirror defines a first and a second focal point, and wherein the first focal point of each of said off-axis ellipsoidal mirrors is coincident upon the flow tube;

a plurality of optical units, each of said optical units located at the second focal point of a corresponding one of said off-axis ellipsoidal mirrors; and a light source producing high-intensity excitation light which is caused to impinge upon said biological material and excite a response therefrom.

2. The optical system of claim 1, further comprising:

an aperture extending through one of said off-axis ellipsoidal mirrors;

wherein said light source is an external light source; and wherein light from said external light source passes through the aperture and impinges upon said biological material.

3. The optical system of claim 2, wherein said external light source is a laser.

4. The optical system of claim 1, further comprising:

a plurality of apertures, each of said apertures extending through a corresponding one of said off-axis ellipsoidal mirrors;

wherein said light source is a plurality of external light sources;

wherein light from each of said external light sources passes through a corresponding one of said apertures and impinges upon said biological material; and wherein each of said external light sources providing a unique excitation wavelength band.

5. The optical system of claim 1 wherein said optical units are multifunction optical units.

6. The optical system of claim 5 wherein at least one of the multifunction optical units contains said light source.

7. The optical system of claim 6 wherein at least one of the multifunction optical units contains an optical detector.

8. The optical system of claim 7 wherein said optical detector is a non-imaging sensor selected from the group consisting of photodiodes and photo-multiplier tubes.

9. The optical system of claim 7 wherein said optical detector is an imaging device selected from the group consisting of: charge coupled devices, complementary metal oxide semiconductor array sensors, and image intensifying tubes.

10. The optical system of claim 1 further comprising:

a plurality of exit ports, exiting said optical mirror enclosure;

wherein each of said exit ports is located at the second focal point of one of said off-axis ellipsoidal mirrors; and a plurality of fiber optic cables, wherein each of said exit ports is coupled to one of said optical units with one of said fiber optic cables.

11. A flow cytometer comprising:

a flow tube, designed to carry biological material suspended in a flowing fluid;

a plurality of off-axis ellipsoidal mirrors forming an optical mirror enclosure and defining an internal mirror cavity, said internal cavity fully surrounding said flow tube, each of said off-axis ellipsoidal mirrors defining a first and a second focal point and the first focal point of each of said off-axis ellipsoidal mirrors is coincident upon the flow tube;

a plurality of multifunction optical units, each of said multifunction optical units located at the second focal point of a corresponding one of said off-axis ellipsoidal mirrors, at least one of said multifunction optical units containing an optical detector; and a light source producing high-intensity excitation light which is caused to impinge upon said biological material and excite an optical response therefrom.

12. The flow cytometer of claim 11 wherein said optical detector is a non-imaging sensor selected from the group consisting of photodiodes and photo-multiplier tubes.

13. The flow cytometer of claim 11 wherein said optical detector is an imaging device selected from the group consisting of charge coupled devices, complementary metal oxide semiconductor array sensors, and image intensifying tubes.

14. The flow cytometer of claim 11, further comprising a common top cover-plate and wherein:

the off-axis ellipsoidal mirrors are compliantly fastened and aligned to a central hub through the use of garter springs; and a bottom surface edge of each of the off-axis ellipsoidal mirrors is spring-loaded such that a top surface edge of each of the off-axis ellipsoidal mirrors bottoms out on said common top cover plate.

15. An ultraviolet light disinfecting system for water, said system comprising:

a flow tube, designed to carry water with biological material suspended therein, and including a first and a second end;

a plurality of off-axis ellipsoidal mirrors forming an optical mirror enclosure and defining an internal mirror cavity, wherein said internal cavity fully surrounds said flow tube and the first and second ends of said flow tube protrude from opposing sides of said optical mirror enclosure, wherein each of said off-axis ellipsoidal mirrors define a first and a second focal point, and wherein the first focal point of each of said off-axis ellipsoidal mirrors is coincident upon the flow tube; and a plurality of optical units, each of said multifunction optical units located at the second focal point of a corresponding one of said off-axis ellipsoidal mirrors and at least of said multifunction optical units including a high-intensity ultraviolet light source.

16. The ultraviolet light disinfecting system for water of claim 15 wherein said high-intensity ultraviolet light source produces ultraviolet light with a wavelength of approximately 260 nanometers.

17. The ultraviolet light disinfecting system for water of claim 15 wherein said high-intensity ultraviolet light source is a low-pressure mercury discharge lamp.

18. The ultraviolet light disinfecting system for water of claim 15 wherein said optical units are multifunction, at least one of the multifunction optical units containing an optical detector.

19. An optical system for use in conjunction with a flowing fluid containing suspended biological material, said optical system comprising:

a flow tube, designed to carry said flowing fluid, and including a first and a second end;

a plurality of off-axis ellipsoidal mirrors forming an optical mirror enclosure and defining an internal mirror cavity, wherein said internal cavity fully surrounds said flow tube and the first and second ends of said flow tube protrude from opposing sides of said optical mirror enclosure, wherein each of said off-axis ellipsoidal mirrors defines a first and a second focal point, wherein the first focal point of each of said off-axis ellipsoidal mirrors is coincident upon the flow tube, and a plurality of optical units, each of said optical units located at the second focal point of a corresponding one of said off-axis ellipsoidal mirrors; and a light source producing high-intensity excitation light which is caused to impinge upon said biological material and excite a response therefrom.

20. An ultraviolet light disinfecting system for water, said system comprising:

a flow tube, designed to carry water with biological material suspended therein, and including a first and a second end;

a plurality of off-axis ellipsoidal mirrors forming an optical mirror enclosure and defining an internal mirror cavity, wherein said internal cavity fully surrounds said flow tube and the first and second ends of said flow tube protrude from opposing sides of said optical mirror enclosure, wherein each of said off-axis ellipsoidal mirrors define a first and a second focal point, wherein the first focal point of each of said off-axis ellipsoidal mirrors is coincident upon the flow tube, and a plurality of optical units, each of said multifunction optical units located at the second focal point of a corresponding one of said off-axis ellipsoidal mirrors and at least of said multifunction optical units including a high-intensity ultraviolet light source.

* * * * *